(12) United States Patent
Hamada et al.

(10) Patent No.: US 11,047,797 B2
(45) Date of Patent: Jun. 29, 2021

(54) RESIN DETERMINATION METHOD AND APPARATUS

(71) Applicant: Panasonic Intellectual Property Management Co., Ltd., Osaka (JP)

(72) Inventors: Shingo Hamada, Osaka (JP); Noriyuki Suzuki, Osaka (JP); Naoya Miyaji, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/664,448

(22) Filed: Oct. 25, 2019

(65) Prior Publication Data

US 2020/0141865 A1     May 7, 2020

(30) Foreign Application Priority Data

Nov. 7, 2018  (JP) ............................. JP2018-209900

(51) Int. Cl.
  *G01N 21/3563*     (2014.01)
  *G01N 21/359*     (2014.01)

(52) U.S. Cl.
  CPC ....... *G01N 21/3563* (2013.01); *G01N 21/359* (2013.01)

(58) Field of Classification Search
  CPC ............. G01N 21/3563; G01N 21/359; G01N 33/442; G01N 2001/2866; G01N 21/55; G01N 2021/3572; Y02W 30/62; B29B 17/02; B29B 2017/0279; B29B 2017/0203; B07C 2501/0054; B07C 5/342; B07C 5/3422
  See application file for complete search history.

(56) References Cited

U.S. PATENT DOCUMENTS

| | | |
|---|---|---|
| 5,703,681 A | 12/1997 | Hoult |
| 6,852,977 B2 | 2/2005 | Hisazumi et al. |
| 7,432,507 B2 | 10/2008 | Iwamoto et al. |
| 9,024,224 B2 | 5/2015 | Mase et al. |
| 2003/0155511 A1 | 8/2003 | Hisazumi et al. |
| 2006/0157650 A1 | 7/2006 | Iwamoto et al. |
| 2010/0243772 A1* | 9/2010 | Kojima ................. B29B 17/02 241/24.11 |
| 2012/0305456 A1 | 12/2012 | Mase et al. |
| 2014/0203177 A1* | 7/2014 | Kinugawa .......... G01N 21/3563 250/339.11 |

(Continued)

FOREIGN PATENT DOCUMENTS

| | | |
|---|---|---|
| EP | 0 819 929 | 1/1998 |
| EP | 3 339 840 | 6/2018 |

(Continued)

*Primary Examiner* — Christine S. Kim
(74) *Attorney, Agent, or Firm* — Wenderoth, Lind & Ponack, L.L.P.

(57) ABSTRACT

Lower surface 2c or upper surface 2d of object to be sorted 2 is processed such that arithmetic mean roughness Ra is not less than 0.025 μm in not less than 50% of lower surface 2c or upper surface 2d, object to be sorted 2 is irradiated with infrared light, and reflected light 4 from lower surface 2c or upper surface 2d of object to be sorted 2 is received, thereby determining a resin type of object to be sorted 2 on the basis of a reflection or absorption spectrum of object to be sorted 2 obtained from reflected light 4.

6 Claims, 7 Drawing Sheets

(56) References Cited

U.S. PATENT DOCUMENTS

2019/0128801 A1\* 5/2019 Hamada ............ G01N 21/3559

FOREIGN PATENT DOCUMENTS

| EP | 3 477 281 | | 5/2019 | |
|----|-----------|---|--------|---|
| EP | 3477281 A1 | \* | 5/2019 | ........... G02B 5/0221 |
| JP | 2002-286637 | | 10/2002 | |
| JP | 2013064726 A | \* | 4/2013 | |
| JP | 6160475 B | | 7/2017 | |
| WO | 01/86267 | | 11/2001 | |
| WO | 2005/015174 | | 2/2005 | |
| WO | 2012/035785 | | 3/2012 | |

\* cited by examiner

RESIN DETERMINATION METHOD AND APPARATUS

BACKGROUND

1. Technical Field

The disclosure relates to a resin determination method and an apparatus for a resin type of an object to be sorted (in other words, an object of resin determination) that is a group of a plurality of types of small pieces.

2. Description of the Related Art

Environmental problems, such as global warming and exhaustion of resources, have occurred on a global scale due to mass consumption and mass disposal-type economic activities.

Under such circumstances, the Home Appliance Recycling Act has been enforced since April in 2001 in Japan for constructing a resource recycling-type society. The Home Appliance Recycling Act requires recycling of used home appliances (such as ACs, TVs, refrigerators, freezers, laundry washing machine, and a clothing driers). Therefore, the used home appliances are crushed into small pieces in home appliance recycling plants, are then sorted into each type of materials, are collected by using magnetic force, wind power, vibration, or the like, are sorted depending on material types, and are changed into resources again as recycle materials. Resin materials such as polypropylene (hereinafter, referred to as PP), polystyrene (hereinafter, referred to as PS), and acrylonitrile butadiene styrene (hereinafter, referred to as ABS) are used in many home appliances and are sorted into each resin type and are collected by sorting apparatuses utilizing light absorbing properties in a near-infrared region based on molecular structures of the resin.

Figure 5:
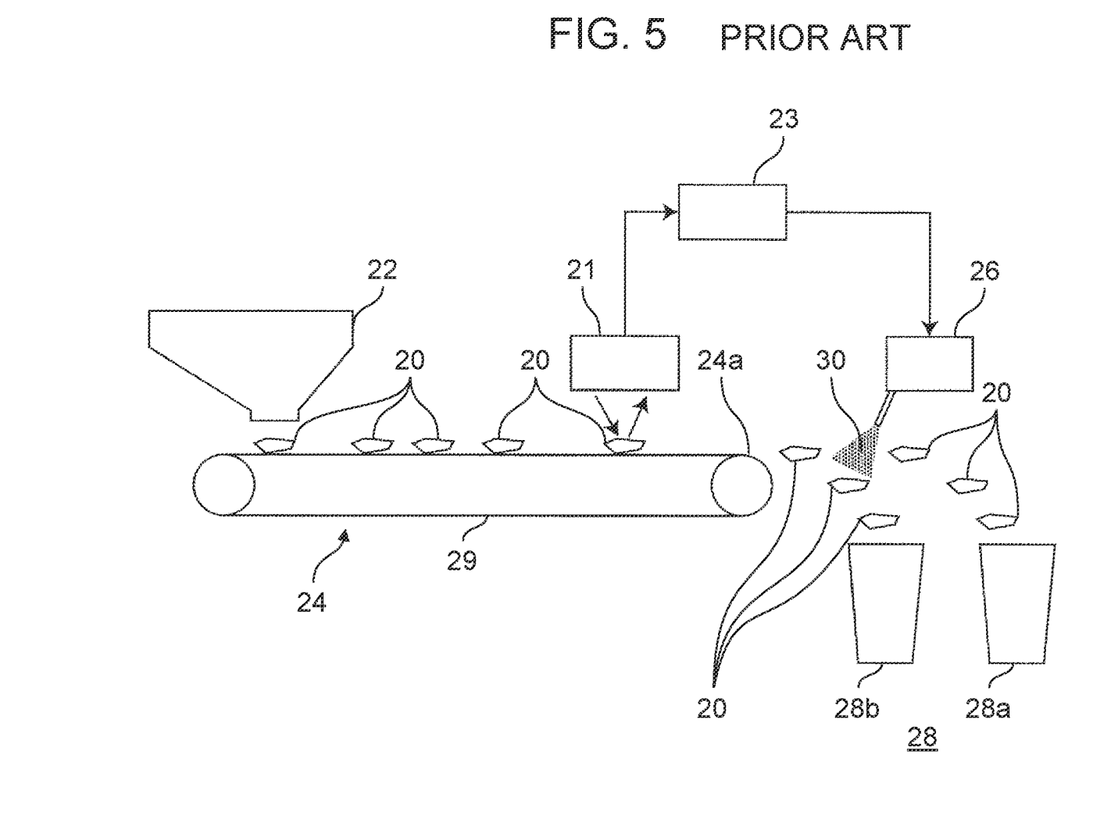
FIG. 5 is a schematic diagram of an apparatus used for resin determination in the related art as disclosed in Japanese Patent No. 6160475.

An apparatus related to changing resin materials into resources again by utilizing the light absorbing properties in an infrared region has been proposed in Japanese Patent No. 6160475. According to the technology disclosed in Japanese Patent No. 6160475, resin flake 20 is supplied from a hopper of flake supplier 22 to flake transporter 24 as illustrated in FIG. 5. Flake transporter 24 has a belt conveyor 29 and transports resin flake 20, which has been supplied from flake supplier 22, to discharge port 24a through a portion below reflectance measurer 21 by belt conveyor 29. Sorted flake resin collector 28 is provided at a position to which resin flake 20 discharged from discharge port 24a falls, and two flake collection containers 28a and 28b are arranged in sorted flake resin collector 28.

Flake discriminator 26 is arranged between discharge port 24a of flake transporter 24 and sorted flake resin collector 28. Flake collection container 28a is arranged at a position to which resin flake 20 discharged from discharge port 24a naturally falls. Flake collection container 28b is arranged at a position that is closer to discharge port 24a than to flake collection container 28a. Flake discriminator 26 causes resin flake 20 to fall into flake collection container 28b using air pressure by blowing air 30 to resin flake 20 discharged from discharge port 24a, for example. Flake discriminator 26 receives an output signal from resin identification unit 23 as a control signal. In a case in which the output signal is a signal indicating an ABS resin, for example, flake discriminator 26 blows air 30 to resin flake 20 discharged from discharge port 24a. Meanwhile, in a case in which the output signal is a signal indicating another resin, flake discriminator 26 does not blow air 30 to resin flake 20 discharged from discharge port 24a.

Note that reflectance measurer 21 includes an irradiation optical system that irradiates resin flake 20 with infrared light and a light receiving optical system for reflected light that receives reflected light from resin flake 20 and guides the reflected light to a light detector. Further, reflectance measurer 21 includes a received light optical system for incident light that switches optical paths as needed and guides infrared light after emission from the irradiation optical system before incidence on resin flake 20 to the light detector.

SUMMARY

According to an aspect of the disclosure, there is provided a resin determination method including:

processing a roughness of a determination target surface of a object to be sorted (in other words, a resin determination target) by a processor to set an arithmetic mean roughness Ra to not less than 0.025 μm in not less than 50% of an area of the determination target surface, the determination target surface being one of (i) an irradiation surface to be irradiated with the infrared light and (ii) a surface opposite to the irradiation surface;

placing the object after being processed by the processor on an object placement surface of a placement unit;

irradiating the object placed on the object placement surface with the infrared light from an irradiator;

receiving reflected light from the object irradiated with the infrared light by a light receiver; and determining a resin type of the object by an arithmetic processor on the basis of a reflection or absorption spectrum obtained from the reflected light received by the light receiver.

According to another aspect of the disclosure, there is provided a resin determination apparatus including:

a processor that processes a roughness of a determination target surface of a object to be sorted (in other words, a resin determination target) to set an arithmetic mean roughness Ra to not less than 0.025 μm in not less than 50% of an area of the determination target surface, the determination target surface being one of (i) an irradiation surface to be irradiated with the infrared light and (ii) a surface opposite to the irradiation surface;

a placement unit that has an object placement surface on which the object after being processed by the processor is placed;

an irradiator that irradiates the object placed on the object placement surface with the infrared light;

a light receiver that is arranged above the object placement surface and receives reflected light from the object irradiated with the infrared light by the irradiator; and an arithmetic processor that determines a resin type of the object on the basis of a reflection or absorption spectrum obtained from the reflected light received by the light receiver.

DETAILED DESCRIPTION

According to the technology disclosed in Japanese Patent No. 6160475, it is possible to determine a resin type since reflected light from resin colored with a white or black color, for example, can be detected. However, there is a problem that a resin type of transparent resin cannot be determined since the transparent resin transmits most parts of the infrared rays.

A resin type of transparent resin cannot be sorted with the infrared rays. Therefore, for resin pieces containing transparent resin, a visible light color hue sorting apparatus is used first to first determine a color for whether or not the resin pieces are transparent. A water specific gravity sorting apparatus is used to sort the resin, which has been determined to be transparent, into a resin such as PP that floats in water and the other resins, for example. To do this, a plurality of apparatuses or processes are required to sort the transparent resin, and there is also a problem that the number of types of transparent resin that can be collected is limited.

The disclosure solves the aforementioned problems in the related art, and an object thereof is to provide resin determination method and apparatus for determining a resin type of a transparent resin using an infrared ray.

Hereinafter, an embodiment of the disclosure will be described in detail with reference to drawings.

Figure 1:
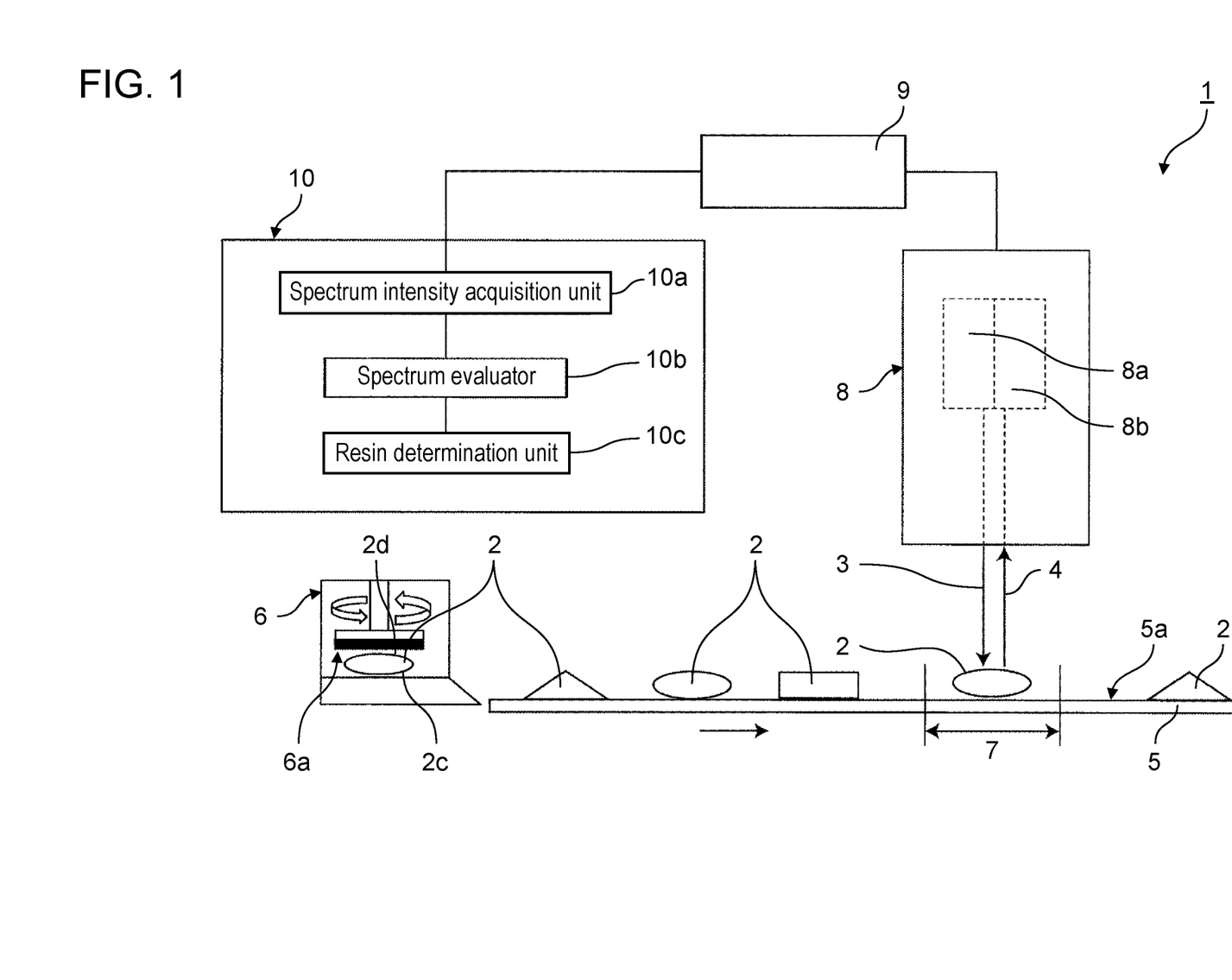
FIG. 1 is a schematic diagram of a resin determination apparatus according to an embodiment of the disclosure.

FIG. 1 is a schematic diagram of resin determination apparatus 1 according to the embodiment.

Resin determination apparatus 1 includes at least processor 6, infrared ray detector 8, arithmetic processor 10, and placement unit 5. Resin determination apparatus 1 performs processing on object to be sorted 2 made of an unknown material (resin type) and determines whether or not object to be sorted 2 is of a predetermined resin type using infrared light. In particular, resin determination apparatus 1 can determine the resin type of object to be sorted 2 even if object to be sorted 2 is a transparent resin. As object to be sorted 2, mainly a resin or a composite of a resin and another substance (such as metal or glass) is conceivable.

Processor 6 has rough surface 6a with arithmetic mean roughness Ra of not less than 1.6 μm.

Infrared ray detector 8 has irradiator 8a and light receiver 8b.

Arithmetic processor 10 performs resin determination through arithmetic processing on the basis of received light information obtained by infrared ray detector 8.

Placement unit 5 has sorted object placement surface 5a on which object to be sorted 2 is placed. That is, the placement surface (for example, lower surface 2c) of object to be sorted 2 is brought into contact with sorted object placement surface 5a. Placement unit 5 is implemented with a belt conveyor, for example.

Processor 6 and infrared ray detector 8 are arranged in order from an upstream side to a downstream side of a transport direction of object to be sorted 2 relative to placement unit 5. As illustrated in FIG. 1, processor 6 is arranged at an end of placement unit 5 on the upstream side of the transport direction in an example. Also, infrared ray detector 8 is arranged in the vicinity of an end of placement unit 5 on the downstream side of the transport direction in an example.

FIG. 1 illustrates an example in which placement unit 5 is a belt conveyor and sorted object placement surface 5a is a belt. It is possible to transport object to be sorted 2 on sorted object placement surface 5a in the transport direction by sorted object placement surface 5a rotating (moving) at a specific speed.

Processor 6 polishes or crushes an upper surface, for example, of object to be sorted 2. Specifically, processor 6 brings object to be sorted 2 into contact with rough surface 6a that rotates or advances and retreats in a forward-backward direction through driving of a motor or the like for a predetermined time, for example, for not less than 3 seconds. Processor 6 is arranged on an upstream side of one end of placement unit 5 along a longitudinal direction. Processor 6 supplies object to be sorted 2 after being subjected to processing to sorted object placement surface 5a at an end of placement unit 5 along the longitudinal direction. Object to be sorted 2 placed on sorted object placement surface 5a by processor 6 is transported by placement unit 5 up to detection region 7 along the longitudinal direction of placement unit 5.

Infrared ray detector 8 includes irradiator 8a that irradiates object to be sorted 2 with irradiation light 3 (for example, infrared light) and light receiver 8b that receives reflected light 4 of irradiation light 3 after being reflected by object to be sorted 2.

Specifically, irradiator 8a is disposed above sorted object placement surface 5a of detection region 7 of placement unit 5. Irradiator 8a irradiates object to be sorted 2 with irradiation light 3 such as infrared light in a state in which not less than 50% of an area of an irradiation surface of object to be sorted 2 on the side of light receiver 8b is a region with arithmetic mean roughness Ra of not less than 0.025 μm. The reason that the proportion of the region is set to be not less than 50% of the area of the irradiation surface is to enhance determination accuracy of arithmetic processor 10. That is, if the proportion of the region is less than 50% of the area of the irradiation surface, it is not possible to secure a spectrum required to reliably determine object to be sorted 2, and there is a probability that detection failure due to erroneous determination may occur. The region in which Ra is 0.025 μm may be the entire irradiation surface, that is, 100% of the area of the irradiation surface. This is also because the surface becomes more like a mirror surface and causes regular reflection, and sufficient reflected light 4 cannot be obtained if arithmetic mean roughness Ra is less than 0.025 μm. An upper limit value of arithmetic mean roughness Ra of the irradiation surface is assumed to be not more than 160 µm for practical use. This is because the surface becomes excessively rough, causes regular reflection in various directions, and sufficient reflected light 4 cannot be obtained if arithmetic mean roughness Ra exceeds 160 µm. Processing may be performed such that arithmetic mean roughness Ra is not less than 0.025 µm in not less than 50% of an area of a surface on the side opposite to the irradiation surface. The surface of object to be sorted 2 processed by the processor 6 will be referred to as a determination target surface. That is, the determination target surface is an irradiation surface which is irradiated with infrared light or a surface on the side opposite to the irradiation surface. Specifically, the determination target surface is upper surface 2d (irradiation surface) or lower surface 2c (the surface on the side opposite to the irradiation surface) of object to be sorted 2 placed on sorted object placement surface 5a of placement unit 5 as illustrated in FIGS. 2B and 2C as will be described later. In other words, the determination target surface is the placement surface of object to be sorted 2 (the surface that is brought into contact with sorted object placement surface 5a, that is, lower surface 2c) or the surface on the side opposite to the placement surface (upper surface 2d). Also, a region in which object to be sorted 2 is irradiated with infrared light and object to be sorted 2 is projected onto sorted object placement surface 5a is assumed to be a projection region. Processing may be performed such that arithmetic mean roughness Ra is not less than 0.025 µm in the surface of object to be sorted 2 on the side of light receiver 8b or the surface on the side opposite to the aforementioned surface corresponding to not less than 50% of the area of the projection region.

To use light absorbing properties of a molecular structure of a resin, irradiation light 3 and reflected light 4 preferably include a band with a wavelength of 1 to 3 µm as an infrared light effective wavelength region.

Light receiver 8b is disposed above sorted object placement surface 5a in detection region 7 on placement unit 5 and receives reflected light 4 from object to be sorted 2 that has been irradiated with infrared light that is irradiation light 3 from irradiator 8a.

Arithmetic processor 10 is connected to light receiver 8b. In the embodiment, arithmetic processor 10 is connected to light receiver 8b via digital data converter 9 in an example.

Digital data converter 9 converts an electrical signal output by infrared ray detector 8 in accordance with reflected light 4 into digital data.

Information regarding received reflected light 4 is input to arithmetic processor 10 from light receiver 8b, and arithmetic processor 10 determines a resin type of object to be sorted 2 on the basis of a reflection or absorption spectrum of object to be sorted 2 obtained from reflected light 4.

More specifically, arithmetic processor 10 has, at least, spectrum intensity acquisition unit 10a, spectrum evaluator 10b, and resin determination unit 10c.

Spectrum intensity acquisition unit 10a calculates and acquires spectrum intensity of the reflection or absorption spectrum of object to be sorted 2 on the basis of reflected light 4 from light receiver 8b, that is, digital data output from digital data converter 9.

Specifically, analog data of reflected light 4 received by light receiver 8b is input first to spectrum intensity acquisition unit 10a of arithmetic processor 10 from light receiver 8b through digital data converter 9. At this time, the digital data converter 9 converts the analog data of reflected light 4 into digital data of reflected light 4, and the digital data of reflected light 4 is input to spectrum intensity acquisition unit 10a.

Spectrum intensity acquisition unit 10a calculates reflection or absorption spectrum of object to be sorted 2 on the basis of input digital data of reflected light 4. Thereafter, spectrum intensity acquisition unit 10a refers to reference data (for example, a table format or a graph format) representing a relationship between the reflection or absorption spectrum and the spectrum intensity, for example, and generates and acquires a spectrum intensity for determining a resin corresponding to the calculated reflection or absorption spectrum. The reference data representing the relationship between the reflection or absorption spectrum and the spectrum intensity is created in advance using samples of known resin types. It is also possible to create the reference data representing the relationship between the reflection or absorption spectrum and the spectrum intensity while determining resin types in some cases.

Spectrum evaluator 10b obtains a plurality of correlation information pieces between the spectrum intensity acquired by spectrum intensity acquisition unit 10a and the spectrum data of one or more resin types acquired in advance. The correlation information is a dimensionless quantity obtained using a correlation coefficient, regression analysis, multivariate analysis, or the like.

Resin determination unit 10c determines correlation information that is not less than a preset threshold value and has the highest correlation in the correlation information of not less than the threshold value from among a plurality of correlation information pieces obtained by spectrum evaluator 10b as a resin type of object to be sorted 2. In a case in which all the correlation information pieces are less than the preset threshold value, it is determined that the resin is of a resin type other than the resin types corresponding to the correlation information or that determination cannot be made. The determined information can be used for the sorting and the like.

Here, an infrared spectrum of transparent resin 2a as an example of object to be sorted 2 obtained in the embodiment of the disclosure will be briefly described with reference to FIGS. 2A to 2E.

Figure 2A:
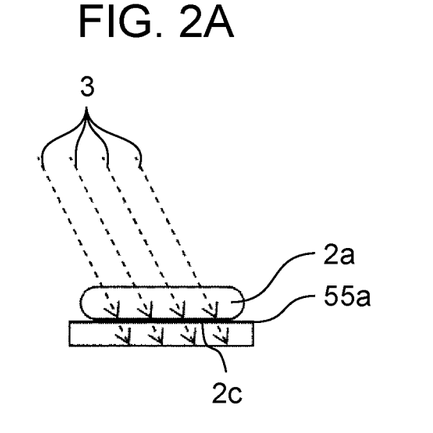
FIG. 2A is a schematic diagram of infrared reflection of a transparent resin according to an embodiment in the related art.
Figure 2B:
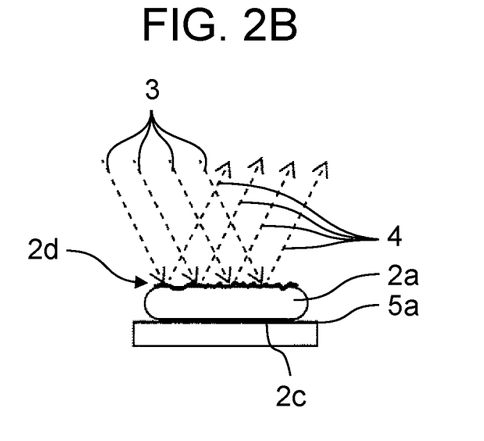
FIG. 2B is a schematic diagram of infrared reflection of a transparent resin according to an embodiment of the disclosure.
Figure 2C:
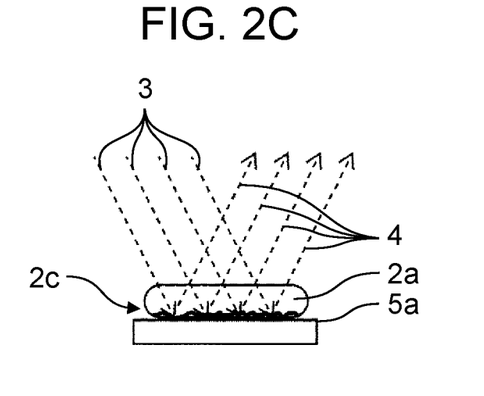
FIG. 2C is a schematic diagram of infrared reflection of a transparent resin according to an embodiment of the disclosure.

FIG. 2A is a schematic diagram of reflection of irradiation light 3 in a case in which transparent resin 2a is placed on sorted object placement surface 55a of a black belt that is typically used using the related art. In FIG. 2A, roughness in lower surface 2c that is a placement surface of transparent resin 2a is not adjusted, and not less than 50% of a projection area of transparent resin 2a on the side of light receiver 8b is not a region in which arithmetic mean roughness Ra is not less than 0.025 µm, for example. Therefore, irradiation light 3 is not reflected by lower surface 2c that is the placement surface of transparent resin 2a, and most parts of irradiation light 3 is transmitted without reflection.

Meanwhile, in FIGS. 2B and 2C, the determination target surface that is upper surface 2d or lower surface 2c of transparent resin 2a is processed such that not less than 50% of the projection area of transparent resin 2a on the side of light receiver 8b is a region with arithmetic mean roughness Ra of not less than 0.025 µm, using the embodiment. Reflected light 4 of irradiation light 3 after being reflected by upper surface 2d or lower surface 2c in a case in which upper surface 2d or lower surface 2c that is a processed surface and also a determination target surface of transparent resin 2a is then irradiated with irradiation light 3 is illustrated in the schematic diagram.

Figure 2D:
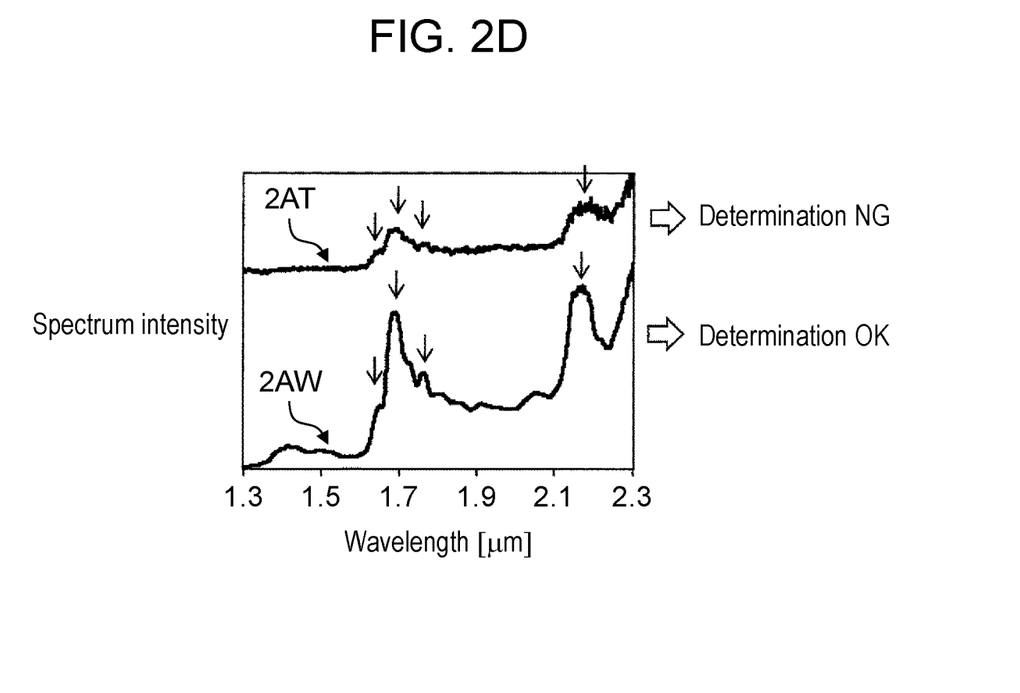
FIG. 2D is a diagram for explaining an infrared spectrum of a resin obtained according to an embodiment in the related art.

FIG. 2D illustrates an infrared spectrum in the related art in which surface is not processed as illustrated in FIG. 2A. In FIG. 2D, an infrared spectrum in a case in which a white polystyrene resin (PS resin) as an example of object to be sorted 2 is placed is represented as "2AW", and an infrared spectrum in a case in which a transparent PS resin as an example of transparent resin 2a is placed is represented as "2AT".

Figure 2E:
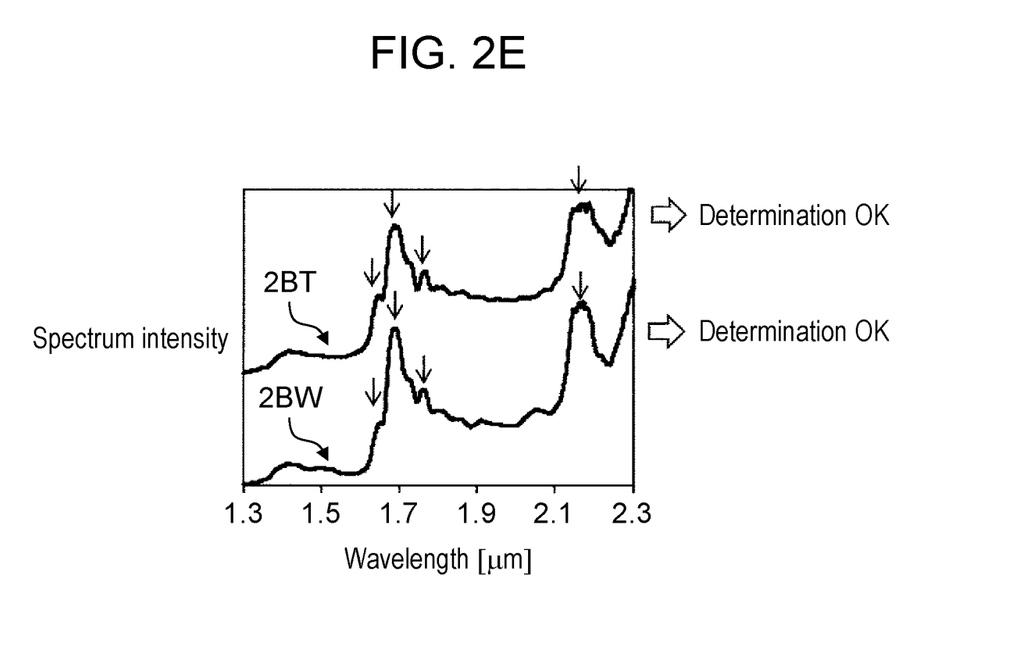
FIG. 2E is a diagram for explaining an infrared spectrum of a resin obtained according to an embodiment of the disclosure.

FIG. 2E illustrates an infrared spectrum according to the disclosure in which the determination target surface has been processed as illustrated in FIGS. 2B and 2C. In FIG. 2E, an infrared spectrum in a case in which a white PS resin as an example of object to be sorted 2 is placed is represented as "2BW", and an infrared spectrum in a case in which a transparent PS resin as an example of transparent resin 2a is placed is represented as "2BT".

In the configuration in FIG. 2A, irradiation light 3 is transmitted through transparent resin 2a, and the infrared light that is irradiation light 3 is absorbed by sorted object placement surface 55a. Therefore, the amount of reflected light 4 from sorted object placement surface 55a is significantly small. Therefore, there is a little change in infrared spectrum "2AT" and it is difficult to determine a resin type for transparent resin 2a that is a transparent PS resin as illustrated as "DETERMINATION NG" in FIG. 2D. However, there is a large change in infrared spectrum "2AW" and it is possible to determine a resin type for object to be sorted 2 that is a white PS resin (not transparent) (see "2AW" in FIG. 2D).

Meanwhile, according to the configuration in FIG. 2B, arithmetic mean roughness Ra is not less than 0.025 μm in not less than 50% of the area of the irradiation surface of transparent resin 2a on the side of light receiver 8b. Therefore, since light is reflected by the determination target surface that is upper surface 2d or lower surface 2c corresponding to the reflection surface of transparent resin 2a without being transmitted therethrough, the amount of reflected light 4 increases. Therefore, it is still possible to obtain a change in infrared spectrum that is close to that of the white PS resin (see "2BW" in FIG. 2E) for the transparent PS resin (see "2BT" in FIG. 2E) as illustrated as "DETERMINATION OK" in FIG. 2E, and it is possible to determine the resin type. At this time, upper surface 2d or lower surface 2c of transparent resin 2a can reflect light regardless of whether or not upper surface 2d or lower surface 2c is in contact with sorted object placement surface 5a as illustrated in FIGS. 2B and 2C. Therefore, it is possible to make determination in a state in which contamination or scratching on sorted object placement surface 5a hardly affect the determination.

Here, examples of processor 6 (61, 64, 63) will be described with reference to FIGS. 3A to 3C.

Figure 3A:
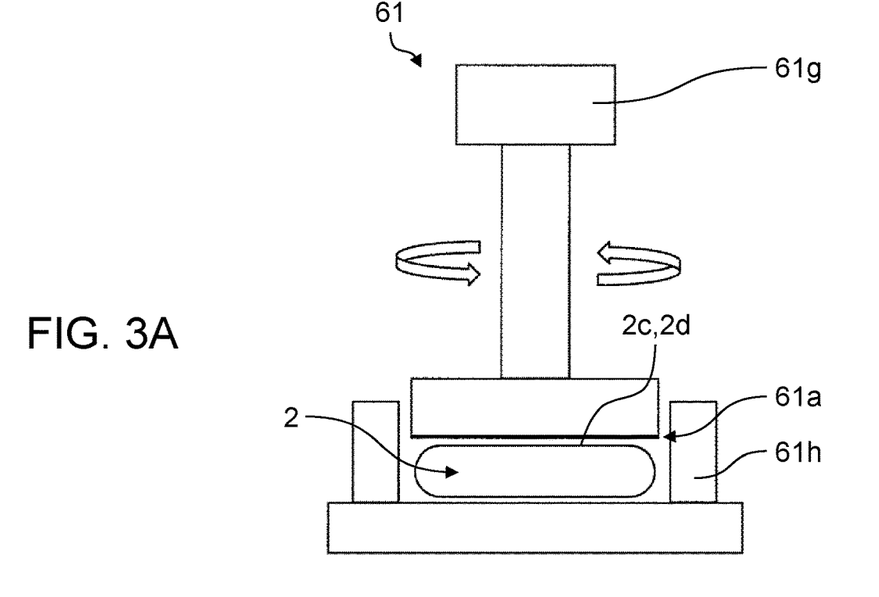
FIG. 3A is a diagram for explaining an example of a processor according to an embodiment of the disclosure.

FIG. 3A is a schematic diagram of a method of polishing or crushing the determination target surface that is upper surface 2d or lower surface 2c of object to be sorted 2 in holding frame 61h by rotating or vibrating rough surface 61a in a planar shape using drive device 61g such as a motor.

Figure 3B:
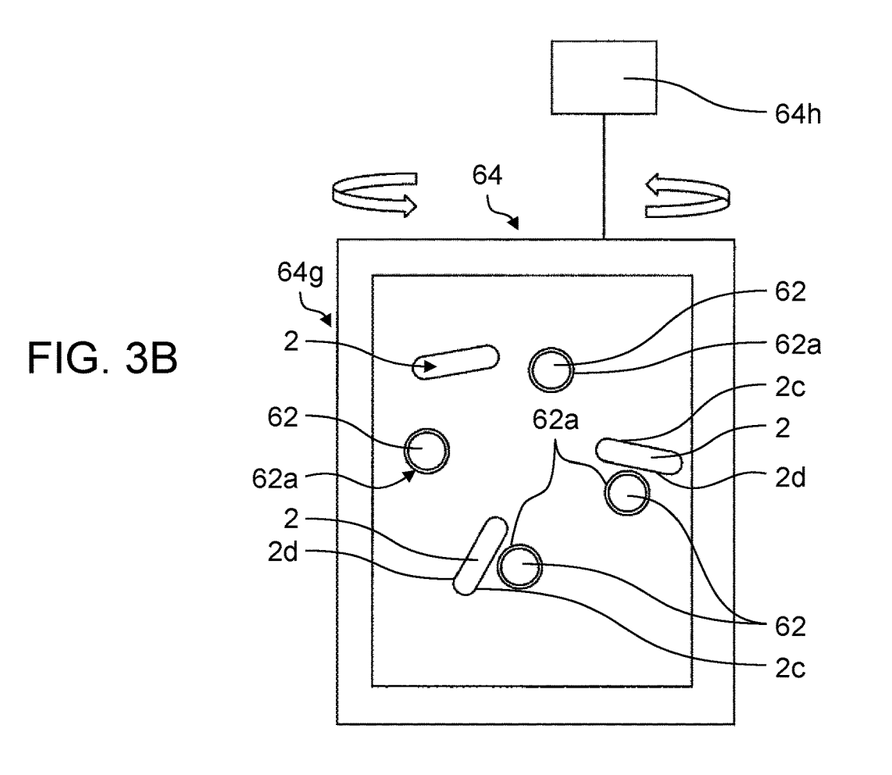
FIG. 3B is a diagram for explaining another example of a processor according to an embodiment of the disclosure.

FIG. 3B is a schematic diagram of a method of polishing or crushing the determination target surface that is upper surface 2d or lower surface 2c of object to be sorted 2 in container 64g, in which the respective surfaces of multiple spherical balls 62 accommodated in closed container 64g are assumed to be rough surfaces 62a.

Figure 3C:
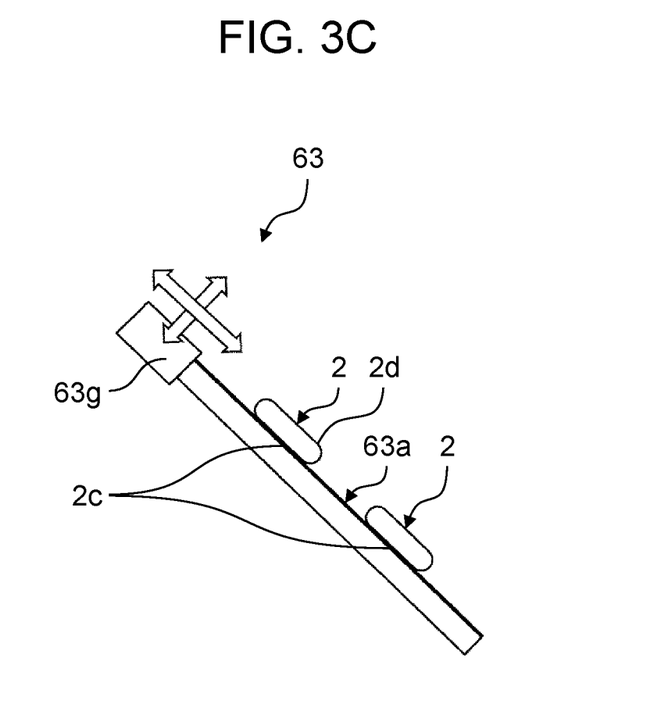
FIG. 3C is a diagram for explaining yet another example of a processor according to an embodiment of the disclosure.

FIG. 3C is a schematic diagram of a method of polishing or crushing the determination target surface that is upper surface 2d or lower surface 2c of object to be sorted 2 on rough surface 63a by vibrating rough surface 63a in a planar shape using drive device 63g such as a motor.

As illustrated in FIG. 3A, processor 61 arranges rough surface 61a in a planar shape so as to be in contact with upper surface 2d or lower surface 2c of object to be sorted 2 and rotates or vibrates rough surface 61a. It is possible to perform polishing or crushing by bringing rough surface 61a to be rotated or vibrated into contact with upper surface 2d or lower surface 2c of object to be sorted 2 for 3 seconds or more. At this time, arithmetic mean roughness Ra in entire rough surface 61a in contact with object to be sorted 2 is preferably not less than 1.6 μm and not more than 160 μm. An upper limit value of a time during which rough surface 61a is brought into contact with upper surface 2d or lower surface 2c of object to be sorted 2 is 10 seconds. This is because there is a high probability that polishing destruction occurs, and object to be sorted 2 is excessively shaved if the contact time exceeds 10 seconds. Surface roughness does not change if the contact time for polishing is elongated. However, if the contact time is excessively long, shaved powder (that is, dust) increases, and the amount of object to be sorted 2 collected decreases since the entire surface is shaved.

As illustrated in FIG. 3B, processor 64 has spherical ball 62 as rough surface 62a. Arithmetic mean roughness Ra of the surface of ball 62 is not less than 1.6 μm and not more than 160 μm. It is possible to bring rough surface 62a into contact with upper surface 2d or lower surface 2c of object to be sorted 2 for 3 seconds or more and to perform polishing or crushing by placing ball 62 and object to be sorted 2 in container 64g and rotating or vibrating entire container 64g using drive device 64h such as a motor. At this time, an inner surface of container 64g is preferably a rough surface with arithmetic mean roughness Ra of not less than 1.6 μm and not more than 160 μm.

Alternatively, processor 63 places object to be sorted 2 such that upper surface 2d or lower surface 2c of object to be sorted 2 is brought into contact with rough surface 63a in a planar shape and applies vibration thereto as illustrated in FIG. 3C. It is possible to perform polishing or crushing by bringing rough surface 63a to which vibration is applied into contact with upper surface 2d or lower surface 2c of object to be sorted 2 for 3 seconds or more. At this time, arithmetic mean roughness Ra in entire rough surface 63a in contact with object to be sorted 2 is preferably not less than 1.6 μm and not more than 160 μm.

If arithmetic mean roughness Ra of rough surface 61a, rough surface 62a, and rough surface 63a is less than 1.6 μm, upper surface 2d or lower surface 2c of object to be sorted 2 hardly becomes a rough surface, and a sufficient reflection spectrum cannot be obtained. Also, in a case in which arithmetic mean roughness Ra of rough surface 61a, rough surface 62a, and rough surface 63a is greater than 160 μm, the rough surface of upper surface 2d and lower surface 2c of object to be sorted 2 becomes excessively rough, and a sufficient reflection spectrum cannot be obtained.

Figure 4:
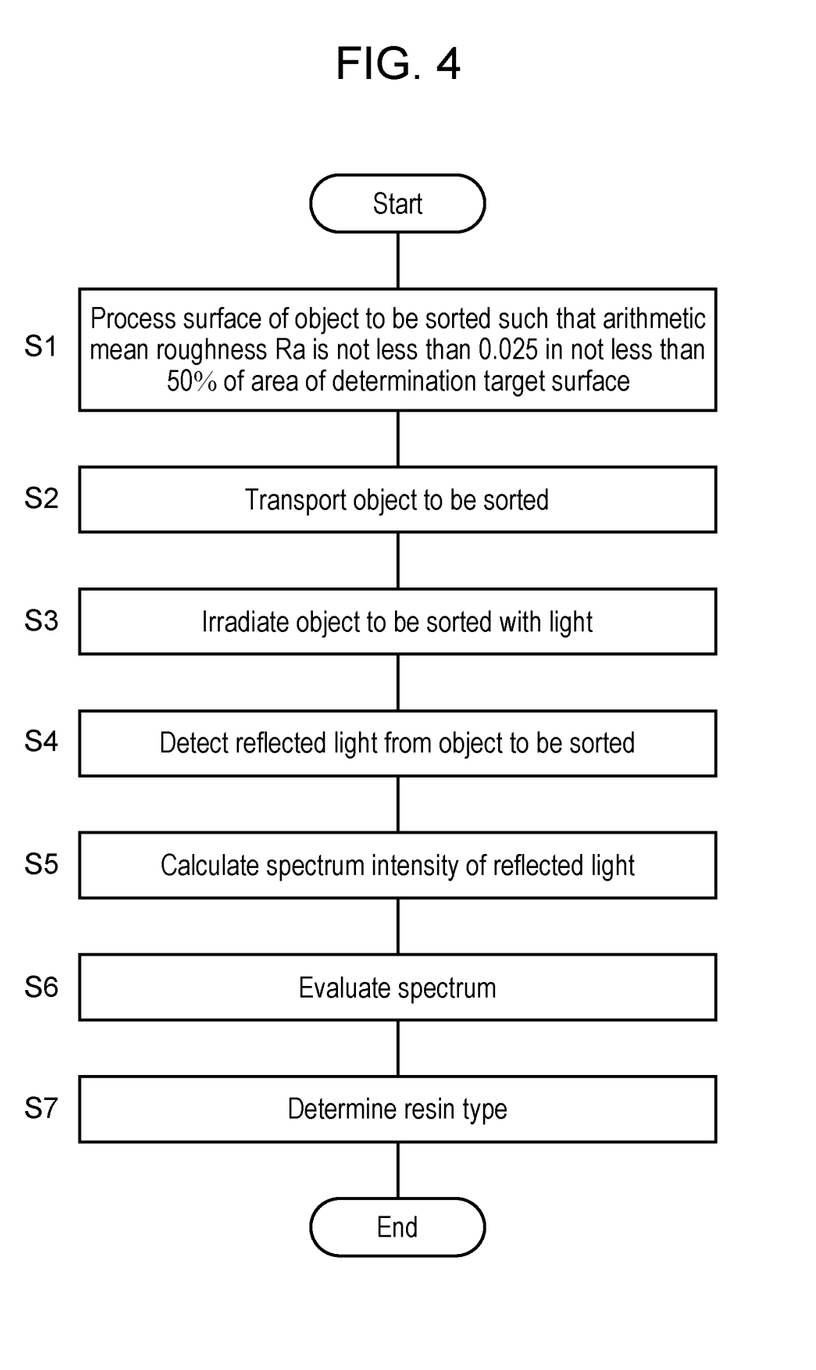
FIG. 4 is a flowchart illustrating a flow in which the resin determination apparatus determines a resin according to an embodiment of the disclosure.

Next, operations of resin determination apparatus 1 in FIG. 1 will be described on the basis of the flowchart in FIG. 4.

First, processor 6 processes the determination target surface of object to be sorted 2 through polishing, crushing, or the like such that arithmetic mean roughness Ra is not less than 0.025 μm in at least not less than 50% of the area of the placement surface (the surface that is brought into contact with sorted object placement surface 5a) or the surface on the side opposite to the placement surface (lower surface 2c or upper surface 2d, for example) of object to be sorted 2 in Step S1. In other words, roughness of at least the determination target surface of the object to be sorted that is the irradiation surface (upper surface 2d) or the surface on the side opposite to the irradiation surface (lower surface 2c) of object to be sorted 2 irradiated with the infrared light is processed to set arithmetic mean roughness Ra to be not less than 0.025 μm in not less than 50% of the area of the determination target surface in Step S1.

Next, object to be sorted 2 is put onto placement unit 5 moving at a specific speed from processor 6, is placed on sorted object placement surface 5a of placement unit 5, and is transported up to detection region 7 in Step S2.

Then, infrared ray detector 8 irradiates object to be sorted 2, which has been placed on sorted object placement surface 5a and has reached detection region 7, with infrared light that is irradiation light 3 from irradiation unit 8a in Step S3.

Next, infrared ray detector 8 detects reflected light 4 from object to be sorted 2 that has reached detection region 7 in Step S4.

Next, analog data of reflected light 4 detected by infrared ray detector 8 is output from infrared ray detector 8 to arithmetic processor 10 through digital data converter 9 in Step S5. Digital data converter 9 converts the analog data of reflected light 4 into digital data of reflected light 4. Spectrum intensity acquisition unit 10a of arithmetic processor 10 calculates a reflection spectrum or an absorption spectrum of object to be sorted 2 on the basis of the input digital data of reflected light 4 and generates spectrum intensity for determining the resin on the basis of the reflection spectrum or the absorption spectrum. The spectrum intensity for determining the resin is output from spectrum intensity acquisition unit 10a to spectrum evaluator 10b.

Next, spectrum evaluator 10b calculates and evaluates a correlation coefficient between spectrum intensity for determining the resin and a sample spectrum as an example of the correlation information on the basis of the spectrum intensity for determining the resin calculated by spectrum intensity acquisition unit 10a and the sample spectrum in Step S6. Here, the sample spectrum is spectrum intensity of a resin with known physical properties that have been acquired in advance. The calculated correlation coefficient is output from spectrum evaluator 10b to resin determination unit 10c.

Next, resin determination unit 10c determines a resin type of object to be sorted 2 on the basis of the correlation coefficient with the sample spectrum and a preset threshold value in Step S7. Specifically, resin determination unit 10c determines a resin type that has a correlation coefficient of not less than the threshold value and is related with the largest correlation coefficient as the resin type of object to be sorted 2.

As described above, according to the resin determination method and apparatus according to the embodiment, polishing or crushing is performed by bringing rough surface 6a of processor 6 with arithmetic mean roughness Ra of not less than 1.6 μm and not more than 160 μm into contact with lower surface 2c or upper surface 2d that is the surface of object to be sorted 2 for a predetermined time, for example, 3 seconds or more. In this manner, arithmetic mean roughness Ra is not less than 0.025 μm in not less than 50% of the area of the projection surface of object to be sorted 2 on the light receiving side. Therefore, it is possible to reflect irradiation light 3 by the determination target surface of object to be sorted 2. Therefore, it is possible to determine a resin type of object to be sorted 2 using infrared light that is irradiation light 3 even if object to be sorted 2 is a transparent resin. Further, since the determination target surface of upper surface 2d or lower surface 2c of object to be sorted 2 can reflect light regardless of whether or not the determination target surface is in contact with sorted object placement surface 5a, contamination or scratching on sorted object placement surface 5a hardly affect the determination, and highly accurate determination can be made. In other words, according to the resin determination method and apparatus of the aforementioned aspects of the disclosure, it is possible to determine a resin type of a transparent resin by receiving infrared light reflected by the determination target surface in a state in which arithmetic mean roughness Ra is not less than 0.025 μm in not less than 50% of the area of the placement surface of the transparent resin as an example of the object to be sorted (in other words, the resin determination target) or the surface on the side opposite to the placement surface.

Any embodiments or modification examples of the aforementioned various embodiments and modification examples can be appropriately combined, thereby achieving the effects thereof. Combinations of the embodiments, combinations of examples, or combinations of the embodiments and the examples can be made, and also, combinations of features in different embodiments or examples can also be made.

It is possible to highly accurately determine a resin type of a transparent resin, in particular, by using the resin determination method and apparatus according to the aforementioned aspects of the disclosure. In the related art, although sorting of a transparent resin with a water specific gravity sorting apparatus, which can be performed regardless of a resin color, is a mainstream, it is necessary to dry the resin, and it is only possible to make determination on the basis of whether or not the resin floats in water. The resin determination method and apparatus can promote further advantageous utilization of resins by solving the problems.

What is claimed is:

1. A resin determination method for determining a resin type of an object to be sorted by irradiating the object with infrared light, the method comprising:
    processing a roughness of a determination target surface of the object by a processor to set an arithmetic mean roughness Ra to not less than 0.025 μm in not less than 50% of an area of the determination target surface, the determination target surface being one of (i) an irradiation surface to be irradiated with the infrared light and (ii) a surface opposite to the irradiation surface;
    placing the object after being processed by the processor on an object placement surface of a placement unit;
    irradiating the object placed on the object placement surface with the infrared light from an irradiator;
    receiving reflected light from the object irradiated with the infrared light by a light receiver; and
    determining the resin type of the object by an arithmetic processor on the basis of a reflection or absorption spectrum obtained from the reflected light received by the light receiver.

2. The resin determination method of claim 1, wherein an effective wavelength region of the infrared light is not less than 1 μm and not more than 3 μm.

3. The resin determination method of claim 1, wherein in the processing performed by the processor on the object, a rough surface with arithmetic mean roughness Ra of not less than 1.6 μm and not more than 160 μm is brought into contact with the determination target surface of the object for a predetermined time.

4. A resin determination apparatus for determining a resin type of an object to be sorted by irradiating the object with infrared light, the apparatus comprising:

a processor that processes a roughness of a determination target surface of the object to set an arithmetic mean roughness Ra to not less than 0.025 μm in not less than 50% of an area of the determination target surface, the determination target surface being one of (i) an irradiation surface to be irradiated with the infrared light and (ii) a surface opposite to the irradiation surface;

a placement unit that has an object placement surface on which the object after being processed by the processor is placed;

an irradiator that irradiates the object placed on the object placement surface with the infrared light;

a light receiver that is arranged above the object placement surface and receives reflected light from the object irradiated with the infrared light by the irradiator; and an arithmetic processor that determines the resin type of the object on the basis of a reflection or absorption spectrum obtained from the reflected light received by the light receiver.

5. The resin determination apparatus of claim 4, wherein an effective wavelength region of the infrared light is not less than 1 μm and not more than 3 μm.

6. The resin determination apparatus of claim 4, wherein the processor has a rough surface with arithmetic mean roughness Ra of not less than 1.6 μm and not more than 160 μm and performs the processing by bringing the rough surface into contact with the determination target surface of the object for a predetermined time.

* * * * *